United States Patent [19]

François et al.

[11] Patent Number: 5,654,293
[45] Date of Patent: Aug. 5, 1997

[54] TOPICAL OIL-IN-WATER EMULSION COMPOSITIONS CONTAINING KETOCONAZOLE AND AN ACETONIDE GLUCOCORTICOSTEROID

[75] Inventors: Marc Karel Jozef François, Kalmthout; Alfons Jeanne Wouters, Beerse, both of Belgium; Gerard Frans Maria Jan Cauwenbergh, Plainsboro, N.J.

[73] Assignee: Janssen Pharmaceutica N.V., Beerse, Belgium

[21] Appl. No.: 448,527

[22] PCT Filed: Jan. 12, 1994

[86] PCT No.: PCT/EP94/00092

§ 371 Date: Jun. 14, 1995

§ 102(e) Date: Jun. 14, 1995

[87] PCT Pub. No.: WO94/16710

PCT Pub. Date: Aug. 4, 1994

[30] Foreign Application Priority Data

Jan. 21, 1993 [EP] European Pat. Off. ............. 93200145

[51] Int. Cl.$^6$ ............. A61K 31/56; A61K 31/58; A61K 31/495; A61K 31/50

[52] U.S. Cl. ............. 514/171; 514/174; 514/252; 514/887

[58] Field of Search ............. 514/252, 174, 514/171, 887

[56] References Cited

U.S. PATENT DOCUMENTS 4,883,792  11/1989  Timmons et al. ............. 514/169

FOREIGN PATENT DOCUMENTS

WO92/18133  10/1992  WIPO.

OTHER PUBLICATIONS

F. Högl et al., "The Influence of Steroids on the Antifungal and Antibacterial *Activities of Imidazole Derivatives*", *MYKOSEN*, vol. 23, No. 8, Aug. 1980, pp. 426-439. (Translation of the article is also included.)

Primary Examiner—William R. A. Jarvis
Attorney, Agent, or Firm—Charles J. Metz

[57] ABSTRACT

The present invention relates to a topical oil-in-water emulsion composition comprising ketoconazole, an acetonide glucocorticosteroid and a dermatologically acceptable carrier, characterized by a pH above 2.5 and below 6, and a method of preparing said composition.

18 Claims, No Drawings

TOPICAL OIL-IN-WATER EMULSION COMPOSITIONS CONTAINING KETOCONAZOLE AND AN ACETONIDE GLUCOCORTICOSTEROID

CROSS-REFERENCE TO RELATED APPLICATIONS

This application is based upon PCT Application Serial No. PCT/EP 94/00092, filed Jan. 12, 1994, which claims priority from European Application Serial No. 93.200.145.6, filed on Jan. 21, 1993.

Mykosen 23(8), 426–439 (1980) reports on the activity of ketoconazole in the presence of triamcinolone acetonide.

WO 92/18133 discloses a liquid aqueous solution containing an antifungal and asteroid for use as a mouthwash.

Glucocorticoid based compositions are being used since a long time to treat inflammations of the skin. On the other hand, ketoconazole compositions have proved to be effective in the treatment of mycotic infections. Skin diseases, however, are often characterized by the combination of both inflammatory conditions and mycotic infections, since the inflammatory processes of the skin create predisposing conditions for the growth and proliferation of pathogenic micro-organisms. A single-drug therapy with an anti-inflammatory or an antifungal agent alone therefore is often insufficient to treat various skin diseases.

Up till now, the preparation of a formulation comprising both ketoconazole and a glucocorticoid was hindered by the destabilization of the steroid in the presence of ketoconazole. The stability problems involved in combining a 17-ester steroid with an imidazole antifungal agent are known from e.g. U.S. Pat. No. 5,002,938.

The present invention provides physicochemically stable compositions for the treatment of skin disorders of various pathologies, which comprise in one formulation both ketoconazole and an acetonide glucocorticosteroid.

The present invention is concerned with topical compositions, comprising ketoconazole, an acetonide glucocorticosteroid and a dermatologically acceptable carrier, characterized by a pH above 2.5 and below 6; the preparation of said compositions; and the use of said compositions for the treatment of inflammations and/or mycotic infections of the skin. The subject compositions are characterized by their dual pharmacological activity, being their anti-microbial and anti-inflammatory action. Unexpectedly, it was found that the anti-inflammatory activity of acetonide glucocorticosteroids, in particular that of desonide, was potentiated in the presence of ketoconazole. Therefore, the present invention is further concerned with the use of ketoconazole as a potentiator of the anti-inflammatory activity of acetonide glucocorticosteroids, in particular that of desonide. As a consequence, a less potent steroid can be used when compared to conventional compositions having a comparable anti-inflammmatory activity, which is likely to reduce the incidence and severity of adverse reactions associated with the topical use of steroids.

Further, the excellent physicochemical stability of the subject compositions is unexpected in view of the prior-art. The term "stable compositions" as used hereinbefore and hereinafter relates to a composition wherein the decrease in the desonide content is below 12%, preferably below 10% and most preferably below 6% after storage for 6 months at 30° C. or below.

Ketoconazole is the generic name of 1-acetyl-4-[4-[2-(2,4-dichlorophenyl)-2imidazol-1-ylmethyl-1,3-dioxolan-4-ylmethoxy]phenyl]piperazine. The term "ketoconazole" as used herein comprises ketoconazole in the free base form, the pharmaceutically acceptable addition salts, the stereochemically isomeric forms thereof and the tautomeric forms thereof. The preferred ketoconazole compound is the ($\pm$)-(cis) form of the free base form.

The acid addition forms may be obtained by reaction of the base form with an appropriate acid. Appropriate acids comprise, for example, inorganic acids such as hydrohalic acids, e.g. hydrochloric or hydrobromic acid; sulfuric acid; nitric acid; phosphoric acid and the like; or organic acids such as, for example, acetic, propanoic, hydroxyacetic, 2-hydroxypropanoic, 2-oxopropanoic, ethanedioic, propanedioic, butanedioic, (Z)-butenedioic, (E)-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. The term addition salt as used hereinabove also comprises the solvates which the compound ketoconazole as well as the salts of ketoconazole, are able to form. Said solvates are meant to be included within the scope of the present invention. Examples of such solvates are, e.g. the hydrates, alcoholates and the like.

Ketoconazole and its preparation and pharmacological properties are known from U.S. Pat. No. 4,335,125. Ketoconazole is an antifungal imidazole agent with a broad spectrum of activity against fungi and yeasts such as Candida spp., Blastomyces dermatitidis, Coccidioides immitis, Cryptococcus neoformans, Histoplasma capsulatum, Paracoccidioides brasiliensis, Malassezia furfur, Aspergillus spp., Sporothrix schenkii, most dermatophytes including Epidermophyton floccosum, Microsporum canis and Trichophyton spp., and some bacteria including Erysipelotrix insidiosa, Staphylococcus hemolyticus and Streptococcus pyogenes.

The term "acetonide glucocorticosteroids" refers to glucocorticosteroids which are characterized by the presence of a cyclic acetal with 2-propanone at the 16 and 17 position of the steroid skeleton. Examples of acetonide glucocorticosteroids are desonide, fluclorinide, fluocinolone acetonide, fluocinonide, flurandrenolide, formocortal, halcinonide, triamcinolone acetonide, and the like. The preferred steroid is desonide.

Hereinafter, the amounts of each of the ingredients in the compositions are expressed as percentages by weight based on the total weight of the formulation. Similarly, ratios are intended to define weight-by-weight ratios.

In the compositions according to the present invention the concentration of ketoconazole may range from 0.5 to 5%, preferably from 1 to 3% and in particular is about 2%. The amount of steroid in the present compositions ranges from 0.01 to 0.1%, preferably from 0.04 to 0.06% and in particular is about 0.05%. Generally, the ratio of the amount of ketoconazole to the amount of steroid ranges from about 5:1 to 500:1 and in particular is about 40:1.

The present compositions may take a wide variety of forms such as, for example, liquid forms, e.g. solutions, emulsions, gels or suspensions in aqueous, alcoholic or oily mediums, such as toilet waters, packs, lotions, skin milks or milky lotions and shampoos; or semi-liquid formulations, e.g. creams, hydrogels, gels, pastes, ointments, salves, tinctures and the like, or solid formulations, e.g. powders. The preferred carrier is an oil-in-water emulsion, in particular comprising a mineral oil and more in particular comprising paraffin oil. The liquid formulations may be packaged advantageously in any dispensing device adapted for topical administration, for example in flacons, bottles or also as a spray, either using an inert compressed gas as a propellant such as nitrogen or carbon dioxide, or alternatively using a pump to provide an aerosol. Solid formulations can be applied to the skin with powder puffs or directly with a cover stick. Alternatively, solid formulations such as granules, tablets or powders may also be dissolved in baths. Semi-liquid formulations can be packaged in suitable, art-known containers such as plastic, glass or ceramic pots, tubes, e.g. PVC-covered aluminum tubes.

In addition to the active ingredients the subject compositions comprise a dermatologically acceptable carrier. Said carrier comprises one or more ingredients having no significant antifungal nor anti-inflammatory activity and being well tolerated when applied, to the skin.

In particular, the present compositions may further comprise various additives such as anti-oxidants, thickening agents, wetting agents, emulsifiers, buffer systems, preservatives, chelating agents, and the like. Examples of anti-oxidants include tocopherol, butyl hydroxyanisole, butyl hydroxytoluene, ascorbyl palmitate, ascorbyl oleate, alkyl gallates, and the like. Preferably butyl hydroxyanisole is used as an anti-oxidant, in a concentration of 0.001 to 0.1%, more in particular in a concentration of 0.002 to 0.01% and most in particular in a concentration of 0.005%. Suitable thickening agents may be, for example, lyophobic agents such as, for example, 1-octadecanol, 1-hexadecanol, glycerol monostearate, beeswax, and the like; or lyophilic agents such as, for example, cellulose derivatives, e.g. sodium carboxymethylcellulose; polyethylene glycol; chitin and the derivatives thereof; poloxamers; clays; natural gums; starch derivatives; and the like. Preferably 1-octadecanol and 1-hexadecanol are used in an amount of 0.25 to 10% each, preferably approximately 4% each. Examples of appropriate wetting agents are polyoxyethylene derivatives of sorbitan esters, e.g. polysorbate 80 (=Tween 80®), polysorbate 20 (=Tween 20®), sodium lauryl sulfate, sodium dioctyl sulfosuccinate, and the like. Suitable emulsifiers are, for example, anionic, cationic or, more preferably, nonionic emulsifiers, such as, for example, sucrose esters; glucose esters; polyoxyethylated fatty esters; polyoxyethylated fatty alcohol ethers; glycerol esters, e.g. glycerol monostearate; sorbitan esters, e.g. sorbitan monopalmitate (=Span 40®), sorbitan monostearate (=Span 60 ®); polyoxyethylene derivatives of sorbitan esters, e.g. polysorbate 40 (=Tween 40®), polysorbate 60 (=Tween 60®), and the like. Preferably Span 60 ® and Tween 60 ® are added in an amount of 2% and 1.5%, respectively. Alternatively, Span 40® and Tween 40® can be used in similar concentrations as for Span 60® and Tween 60®. Buffer systems comprise mixtures of appropriate amounts of an acid such as phosphoric, succinic, tartaric, lactic, or preferably citric acid, and a base, in particular sodium hydroxide or disodium hydrogen phosphate. Said buffer systems should maintain the pH of the formulation above 2.5 and below 6, preferably within the range of 3 to 5, more preferably within the range 3.5 to 4.5. Preservatives which can be employed in the present composition to prevent deterioration by microorganisms comprise benzoic acid, sorbic acid, methylparaben, propylparaben, imidazolidinyl ureum derivatives, e.g. Germall 115® and Germall II®, formaldehyde and formaldehyde donors, phenoxetol, benzyl alcohol, quaternary compounds, e.g. benzylalkoninm chloride, and the like. Optionally, the activity of the above preservatives may be enhanced by the addition of 1,2-propanediol, which also displays humectant action. Preferably, benzoic acid and 1,2-propanediol are used in an amount of approximately 0.2% and 10% respectively. Suitable chelating agents are, for example, EDTA and the like. Optionally, a colouring agent is added to the composition such as, for example, Allura Red AC (disodium 6-hydroxy-5-(6-methoxy-4-sulphonato-m-tolylazo) naphthalene-2-sulphonate), Canthaxanthin (β,β-Carotene-4,4'-dione), Sunset Yellow FCF (disodium 6-hydroxy-5-(4-sulphonatophenylazo)naphthalene-2-sulphonate) and the like. Further, the composition may comprise a perfume or another agent to produce a particular smell and/or one or more pigments such as zinc oxide, kaolin, iron oxide, and the like.

Preferred compositions comprise by weight based on the total weight of the composition:
(a) 0.5 to 5% ketoconazole;
(b) 0.01 to 0.1% desonide;
(c) 0.5 to 20% thickening agent;
(d) 0.5 to 10% emulsifier;
(e) 0.001 to 0.1% anti-oxidant;
(f) 0.05 to 0.5% wetting agent;
(g) buffer to maintain the pH of the composition above 2.5 and below 6;
(h) sufficient dermatologically acceptable preservatives to prevent degradation of the composition;
(i) 0.5 to 50% of a dermatologically acceptable oil; and
(j) water.

Particularly preferred compositions are those wherein:
the amount of ketoconazole is 1 to 3%;
the amount of desonide is 0.04 to 0.06%;
the amount of thickening agent is 5 to 10%;
the amount of emulsifier is 1 to 5%;
the amount of anti-oxidant is 0.002 to 0.01%; and
the amount of wetting agent is 0.05 to 0.2%.

The most preferred compositions comprise approximately by weight based on the total weight of the composition:
(a) 2% ketoconazole
(b) 0.05% desonide;
(c) 4% 1-octadecanol and 4% 1-hexadecanol;
(d) 2% Span 60® and 1.5% Tween 60®;
(e) 0.005% butyl hydroxyanisol;
(f) 0.1% Tween 80®;
(g) 2.4% citric acid and 2.5% disodium hydrogen phosphate;
(h) 0.2% benzoic acid and 10% 1,2-propanediol;
(i) 1% paraffin oil;
(j) water; and
(k) 0.00005% Allura Red AC.

To prepare the pharmaceutical compositions of this invention, an effective amount of the active ingredients is combined in intimate admixture with the dermatologically acceptable carrier. Preferably, the carrier formulation is prepared separately and the active ingredients are then added thereto. In a further preferred mode, the preparation of the subject compositions comprises the following steps:
(1) the preservatives are mixed with a fraction of the water phase upon heating to a temperature between 50° C. and 100° C., preferably between 70° C. and 90° C.;
(2) the thickening agents, the emulsifiers, the anti-oxidants and the oil phase are mixed upon heating to a temperature between 65° C. and 90° C., preferably between 75° C. and 80° C.;

(3) the phases prepared in steps (1) and (2) are homogenized and cooled to a temperature below 50° C., preferably below 40° C.;

(4) the wetting agents, the buffer substances and, optionally, the colouring agents are dissolved in the remaining fraction of the water phase and then the active ingredients are suspended therein upon stirring;

(5) the phases prepared in steps (3) and (4) are homogenized and cooled to ambient temperature.

Preferably, the above procedure is conducted under an inert atmosphere, e.g. nitrogen or oxygen-free argon. Optionally, ketoconazole and/or the corticosteroid may be added to the carrier formulation by introduction of the respective powders into the container with the carrier formulation under vacuo. Further, it may be advantageous to use micronized forms of the active ingredients to increase the contact surface of the drug with the skin. Micronized forms can be prepared by micronization techniques known in the art, e.g. by milling in appropriate mills and sieving through appropriate sieves.

Further, the subject compositions advantageously are stored at reduced temperatures, preferably below 15° C., more preferably between 4° and 8° C.

In a further aspect, the present invention is concerned with the use of the compositions as defined hereinabove for the topical treatment of inflammations of the skin and/or mycotic infections thereof. The present compositions may be used in the treatment of, for example, contact dermatitis, atopic dermatitis, eczema, seborrhoeic dermatitis, intertrigo, pruritus, sunburn and the like.

The present invention is also concerned with a method of preventing, reducing or curing inflammations and/or mycotic infections of the skin of warm-blooded animals, in particular human beings, which comprises administering topically to the skin of said warm-blooded animals a composition as defined hereinabove, in an amount effective in preventing, reducing or curing the inflammations and/or mycotic infections of the skin. Moreover, the present invention relates to a product containing ketoconazole and an acetonide glucocorticosteroid, particularly desonide, as a preparation for simultaneous, separate or sequential use in anti-inflammatory and/or anti-mycotic therapy. Such products may comprise, for example, a kit comprising a container with a suitable composition containing ketoconazole and another container containing a composition with an acetonide glucocorticosteroid, particularly desonide. Such a product may have the advantage that a physician who opts for a combined anti-mycotic and anti-inflammatory therapy, can select the appropriate amounts of each component and the sequence and timing of the administration thereof.

The subject compositions should be applied topically, by covering the affected and immediately surrounding area. In general it is contemplated that an effective dosage of the subject compositions would be a treatment of about once to three times daily for about 1 to 21 days. It is evident that said effective dosage may be lowered or increased depending on the response of the treated subject and/or depending on the evaluation of the physician prescribing the compositions of the instant invention. The effective dosage mentioned hereinabove is therefore a guideline only and is not intended to limit the scope or use of the invention to any extent.

The following examples are intended to illustrate the scope of the present invention in all its aspects and not to limit it thereto.

EXAMPLE 1

| F1 | Ingredient | Quantity, mg/g cream |
|---|---|---|
| | ketoconazole | 20 |
| | desonide microfine | 0.5 |
| | 1,2-propanediol | 100 |
| | 1-octadecanol | 40 |
| | 1-hexadecanol | 40 |
| | Span 60 ® | 20 |
| | Tween 60 ® | 15 |
| | paraffin oil | 10 |
| | Tween 80 ® | 1 |
| | butyl hydroxyanisol | 0.05 |
| | citric acid | 2.372 |
| | disodium hydrogen phosphate | 2.476 |
| | benzoic acid | 2 |
| | Allura Red AC | 0.0005 |
| | purified water | q.s. ad 1 g |

Procedure:

(1) In a processor under nitrogen atmosphere, 100 mg 1,2-propanediol and 680 mg purified water were heated to about 70° C.

(2) In another recipient, 113 mg purified water was heated to a temperature between 90° C. and 100° C. and 2 mg benzoic acid was dissolved therein upon stirring.

(3) The aqueous fractions (1) and (2) were homogenized under nitrogen atmosphere.

(4) In another recipient, 40 mg 1-octadecanol, 40 mg 1-hexadecanol, 20 mg Span 60®, 15 mg Tween 60®, 10 mg paraffin oil and 0.05 mg butyl hydroxyanisol were stirred at about 75° C. for about 15 minutes under nitrogen flushing.

(5) Then, the water fraction (3) and the oil fraction (4) were homogenized under nitrogen atmosphere and the mixture was cooled upon stirring to about 35° C.

(6) In a separate recipient, 53 mg purified water was flushed with nitrogen for 30 minutes. Then, 1 mg Tween 80 ®, 2.476 mg disodium hydrogen phosphate, 2.372 mg citric acid and 0.0005 mg Allura Red AC were dissolved therein upon stirring under a nitrogen atmosphere. Then, 20 mg ketoconazole microfine and 0.5 mg desonide microfine were suspended therein upon stirring under a nitrogen atmosphere.

(7) Finally, the aqueous phase (6) comprising the active ingredients was added to the carrier emulsion (5) under a nitrogen atmosphere. The resulting emulsion was cooled to about 20° C. upon stirring under nitrogen flushing.

In a similar way there were prepared:

| | Ingredient | Quantity, mg/g cream |
|---|---|---|
| F2 | | |
| | ketoconazole | 20 |
| | desonide microfine | 0.525 |
| | 1,2-propanediol | 100 |
| | 1-octadecanol | 40 |
| | 1-hexadecanol | 40 |
| | Span 60 ® | 20 |
| | Tween 60 ® | 15 |
| | paraffin oil | 10 |
| | Tween 80 ® | 1 |
| | butyl hydroxyanisol | 0.05 |
| | citric acid | 2.372 |
| | disodium hydrogen phosphate | 2.476 |
| | benzoic acid | 2 |
| | Allura Red AC | 0.0005 |
| | purified water | q.s. ad 1 g |

| Ingredient | Quantity, mg/g cream |
|---|---|
| F3 | |
| ketoconazole | 20 |
| desonide microfine | 0.55 |
| 1,2-propanediol | 100 |
| 1-octadecanol | 40 |
| 1-hexadecanol | 40 |
| Span 60 ® | 20 |
| Tween 60 ® | 15 |
| paraffin oil | 10 |
| Tween 80 ® | 1 |
| butyl hydroxyanisol | 0.05 |
| citric acid | 2.372 |
| disodium hydrogen phosphate | 2.476 |
| benzoic acid | 2 |
| Allura Red AC | 0.0005 |
| purified water | q.s. ad 1 g |
| F4 | |
| ketoconazole | 20 |
| desonide | 0.5 |
| mineral oil | 10 |
| 1-octadecanol | 75 |
| 1-hexadecanol | 50 |
| butyl hydroxyanisol | 0.05 |
| methylparaben | 1.8 |
| propylparaben | 0.2 |
| citric acid | 2.6 |
| dipotassium hydrogen phosphate | 2.2 |
| Tween 80 ® | 1 |
| Span 60 ® | 20 |
| Tween 60 ® | 15 |
| 1,2-propanediol | 100 |
| sodium hydroxide | q.s. ad pH 4.5 |
| purified water | q.s. ad 1 g |
| F5 | |
| ketoconazole | 20 |
| desonide | 0.5 |
| 1,2-propanediol | 100 |
| 1-octadecanol | 75 |
| 1-hexadecanol | 50 |
| butyl hydroxyanisol | 0.05 |
| methylparaben | 1.8 |
| propylparaben | 0.2 |
| citric acid | 2.47 |
| disodium hydrogen phosphate | 3.33 |
| Tween 80 ® | 1 |
| Span 60 ® | 20 |
| Tween 60 ® | 15 |
| paraffin oil | 10 |
| purified water | q.s. ad 1 g |
| F6 | |
| ketoconazole | 20 |
| desonide | 0.5 |
| 1,2-propanediol | 100 |
| 1-octadecanol | 75 |
| 1-hexadecanol | 50 |
| butyl hydroxyanisol | 0.05 |
| methylparaben | 1.8 |
| propylparaben | 0.2 |
| citric acid | 1.06 |
| disodium hydrogen phosphate | 1.87 |
| Tween 80 ® | 1 |
| Span 60 ® | 20 |
| Tween 60 ® | 15 |
| paraffin oil | 10 |
| purified water | q.s. ad 1 g |
| F7 | |
| ketoconazole | 20 |
| desonide | 0.5 |
| 1,2-propanediol | 100 |
| 1-octadecanol | 75 |
| 1-hexadecanol | 50 |
| butyl hydroxyanisol | 0.05 |
| methylparaben | 1.8 |
| propylparaben | 0.2 |
| citric acid | 0.91 |
| disodium hydrogen phosphate | 2.07 |
| Tween 80 ® | 1 |
| Span 60 ® | 20 |
| Tween 60 ® | 15 |
| paraffin oil | 10 |
| purified water | q.s. ad 1 g |

EXAMPLE 2

The table hereinbelow summarizes the decrease in desonide concentration (in %) that was measured upon storage of several ketoconazole-desonide cream formulations and the commercially available desonide (0.1%) composition Sterax® for a period up to 6 months and at a temperature up to 30° C.

| | | % decrease of desonide | | | | | | | |
|---|---|---|---|---|---|---|---|---|---|
| | months | F1 pH = 3.8 | F2 pH = 3.8 | F3 pH = 3.8 | F4 pH = 4.5 | F5 pH = 5 | F6 pH = 5.5 | F7 pH = 6 | Sterax ® pH = 6.9 |
| RT (±22° C.) | 1 | | | | 0.5 | 1.8 | 3.1 | 4.6 | |
| | 2 | | | | 0.4 | | | | |
| | 3 | | | | | 4.1 | 7.5 | 9.7 | 4.0 |
| | 6 | | | | | 3.5 | 9.5 | 14.1 | 0 |
| 25° C. | 6 | 5.3 | 3.4 | 5.4 | | | | | |
| 30° C. | 1 | | | | 1.9 | 1.1 | 5.6 | 7.0 | |
| | 2 | | | | 2.2 | | | | |
| | 3 | 5.6 | 3.4 | 2.1 | | 5.0 | 8.8 | 17.5 | |
| | 6 | 5.3 | | | | 10.7 | 9.9 | 24.5 | 0 |

It is clear that the compositions of pH below 6 show a decrease in desonide concentration which is less than 12% under any of the described circumstances.

We claim:

1. A topical pharmaceutical composition in the form of an oil-in-water emulsion comprising ketoconazole, an acetonide type glucocorticosteroid and a dermatologically acceptable carrier, characterized by a pH above 2.5 and below 6.

2. A composition according to claim 1 wherein the glucocorticosteroid is desonide.

3. A composition according to claim 1 having a pH between 3 and 5.

4. A composition according to claim 2 wherein the ratio of the amount of ketoconazole to the amount of desonide ranges from 5:1 to 500:1.

5. A composition according to claim 1 wherein the dermatological carrier comprises water, a dermatologically acceptable oil and a buffer to maintain the pH of the composition above 2.5 and below 6.

6. A composition according to claim 1 wherein the dermatological carrier comprises a thickening agent, an emulsifier, an anti-oxidant and a wetting agent.

7. A composition according to claim 1 comprising approximately
    (a) 0.5 to 5% ketoconazole;
    (b) 0.01 to 0.1% desonide;
    (c) 0.5 to 20% thickening agent;
    (d) 0.5 to 10% emulsifier;
    (e) 0.001 to 0.1% anti-oxidant;
    (f) 0.05 to 0.5% wetting agent;
    (g) buffer to maintain the pH of the composition above 2.5 and below 6;
    (h) sufficient dermatologically acceptable preservatives to prevent degradation of the composition;
    (i) 0.5 to 50% of a dermatologically acceptable oil; and
    (j) water.

8. A composition according to claim 7 wherein
    the amount of ketoconazole is 1 to 3%;
    the amount of desonide is 0.04 to 0.06%;
    the amount of thickening agent is 5 to 10%;
    the amount of emulsifier is 1 to 5%;
    the amount of anti-oxidant is 0.002 to 0.01%; and
    the amount of wetting agent is 0.05 to 0.2%.

9. A composition according to claim 1 comprising approximately
    (a) 2% ketoconazole
    (b) 0.05% desonide;
    (c) 4% 1-octadecanol and 4% 1-hexadecanol;
    (d) 2% sorbitan monostearate and 1.5% polysorbate 60;
    (e) 0.005% butyl hydroxyanisol;
    (f) 0.1% polysorbate 80;
    (g) 2.4% citric acid and 2.5% disodium hydrogen phosphate;
    (h) 0.2% benzoic acid and 10% 1,2-propanediol;
    (i) 1% paraffin oil;
    (j) water; and
    (k) 0.00005% FD&C Red No. 40.

10. Method for the treatment of inflammatory conditions of the skin, or mycotic skin infections, or both, which comprises the topical administration to the affected skin of the composition of claim 1.

11. Method for the treatment of inflammatory conditions of the skin, or mycotic skin infections, or both, which comprises the topical administration to the affected skin of the composition of claim 2.

12. Method for the treatment of inflammatory conditions of the skin, or mycotic skin infections, or both, which comprises the topical administration to the affected skin of the composition of claim 3.

13. Method for the treatment of inflammatory conditions of the skin, or mycotic skin infections, or both, which comprises the topical administration to the affected skin of the composition of claim 4.

14. Method for the treatment of inflammatory conditions of the skin, or mycotic skin infections, or both, which comprises the topical administration to the affected skin of the composition of claim 9.

15. Method for the treatment of inflammatory conditions of the skin, or mycotic skin infections, or both, which comprises the topical administration to the affected skin of the composition of claim 6.

16. Method for the treatment of inflammatory conditions of the skin, or mycotic skin infections, or both, which comprises the topical administration to the affected skin of the composition of claim 7.

17. Method for the treatment of inflammatory conditions of the skin, or mycotic skin infections, or both, which comprises the topical administration to the affected skin of the composition of claim 8.

18. Method for the treatment of inflammatory conditions of the skin, or mycotic skin infections, or both, which comprises the topical administration to the affected skin of the composition of claim 9.

* * * * *